United States Patent
Barniak et al.

(10) Patent No.: US 12,097,295 B2
(45) Date of Patent: Sep. 24, 2024

(54) PACKAGING SOLUTIONS

(71) Applicant: Bausch + Lomb Ireland Limited, Dublin (IE)

(72) Inventors: Vicki Barniak, Fairport, NY (US); Catherine Scheuer, West Henrietta, NY (US); Ruth Julian, Rochester, NY (US); William T. Reindel, Webster, NY (US); Erning Xia, Penfield, NY (US)

(73) Assignee: BAUSCH + LOMB IRELAND LIMITED, Dublin (IE)

( * ) Notice: Subject to any disclaimer, the term of this patent is extended or adjusted under 35 U.S.C. 154(b) by 248 days.

(21) Appl. No.: 17/398,556

(22) Filed: Aug. 10, 2021

(65) Prior Publication Data
US 2022/0040367 A1 Feb. 10, 2022

Related U.S. Application Data

(60) Provisional application No. 63/063,715, filed on Aug. 10, 2020.

(51) Int. Cl.
*A61L 12/14* (2006.01)
*B65B 55/06* (2006.01)
*B65B 55/22* (2006.01)

(52) U.S. Cl.
CPC ............ *A61L 12/147* (2013.01); *B65B 55/06* (2013.01); *B65B 55/22* (2013.01)

(58) Field of Classification Search
CPC .................................................. A61L 12/147
See application file for complete search history.

(56) References Cited

U.S. PATENT DOCUMENTS

| | | |
|---|---|---|
| 3,408,429 A | 10/1968 | Wichterle |
| 3,660,545 A | 5/1972 | Wichterle |
| 4,113,224 A | 9/1978 | Clark et al. |
| 4,136,250 A | 1/1979 | Mueller et al. |
| 4,143,949 A | 3/1979 | Chen |
| 4,153,641 A | 5/1979 | Deichert et al. |
| 4,197,266 A | 4/1980 | Clark et al. |
| 4,312,575 A | 1/1982 | Peyman et al. |
| 4,555,732 A | 11/1985 | Tuhro |
| 4,740,533 A | 4/1988 | Su et al. |
| 4,910,277 A | 3/1990 | Bambury et al. |
| 4,954,587 A | 9/1990 | Mueller |
| 5,010,141 A | 4/1991 | Mueller |
| 5,034,461 A | 7/1991 | Lai et al. |
| 5,070,215 A | 12/1991 | Bambury et al. |
| 5,079,319 A | 1/1992 | Mueller |
| 5,260,000 A | 11/1993 | Nandu et al. |
| 5,271,876 A | 12/1993 | Ibar |
| 5,310,779 A | 5/1994 | Lai |
| 5,321,108 A | 6/1994 | Kunzler et al. |
| 5,358,995 A | 10/1994 | Lai et al. |
| 5,387,662 A | 2/1995 | Kunzler et al. |
| 5,449,729 A | 9/1995 | Lai |
| 5,464,667 A | 11/1995 | Kohler et al. |
| 5,512,205 A | 4/1996 | Lai |
| 5,610,252 A | 3/1997 | Bambury et al. |
| 5,616,757 A | 4/1997 | Bambury et al. |
| 5,708,094 A | 1/1998 | Lai et al. |
| 5,710,302 A | 1/1998 | Kunzler et al. |
| 5,714,557 A | 2/1998 | Kunzler et al. |
| 5,908,906 A | 6/1999 | Kunzler et al. |
| 6,517,933 B1 | 2/2003 | Soane et al. |
| 9,309,357 B2 | 4/2016 | Awasthi et al. |
| 2003/0044468 A1 | 3/2003 | Cellesi et al. |
| 2008/0096966 A1* | 4/2008 | Burke .................. A61K 9/0048 514/561 |
| 2008/0307751 A1* | 12/2008 | Newman .............. C11D 3/0078 53/425 |
| 2013/0005805 A1* | 1/2013 | Gallois-Bernos ....... A61P 27/02 514/529 |
| 2013/0177599 A1 | 7/2013 | Bowman et al. |
| 2020/0000954 A1* | 1/2020 | Awasthi ............... A45C 11/005 |

FOREIGN PATENT DOCUMENTS

| | | |
|---|---|---|
| WO | 9406485 A1 | 3/1994 |
| WO | 9631792 A1 | 10/1996 |
| WO | PCT/EP2021/072140 | 11/2021 |

OTHER PUBLICATIONS

Dyah et al., "Enhanced Potential of Therapeutic Applications of Curcumin Using Solid-in-Water Nanodispersion Technique", Journal of Chemcial Engineering of Japan, Jan. 20, 2019, pp. 138-143, vol. 52, No. 1.
Sarah Carnell, Thesis, Mar. 1, 2014, pp. 58-60.
Lai, Yu-Chin, "The Role of Bulky Polysiloxanylalkyl Methacryates in Polyurethane-Polysiloxane Hydrogels," Journal of Applied Polymer Science, 1996, pp. 1193-1199, vol. 60.
A.T. Bell, "Chemical Reaction in Nonequilibrium Plasmas", Proc. Intl. Conf. Phenom. Ioniz. Gases, 1977, pp. 19-33.
J. M. Tibbitt et al., "A Model for the Kinetics of Plasma Polymerization", Macromolecules, 1977, 3, pp. 648-653.
M. Tibbitt et al., "Structural Characterization of Plasma-Polymerized Hydrocarbons", J. Macromol. Sci.-Chem., 1976, A10, pp. 1623-1648.

(Continued)

*Primary Examiner* — Donald R Spamer
(74) *Attorney, Agent, or Firm* — Michael E. Carmen; John E. Thomas

(57) ABSTRACT

A packaging system for the storage of an ophthalmic device is disclosed. The packaging system comprises a sealed container containing one or more unused ophthalmic devices immersed in an aqueous packaging solution comprising (a) one or more osmoprotectants, (b) one or more poloxamer comfort agents and (c) one or more polyol demulcents, wherein the aqueous packaging solution has an osmolality of at least about 150 mOsm/kg, a pH of about 6 to about 9 and is heat sterilized.

22 Claims, No Drawings

(56) References Cited

OTHER PUBLICATIONS

C. P. Ho, et al., "Ultrathin coating of plasma polymer of methane applied on the surface of silicone contact lenses", Mater. Res., 1988, 22, 919-937.
H. Kobayashi et al., "Plasma Polymerization of Saturated and Unsaturated Hydrocarbons", Macromolecules, 1974, 3, pp. 277-283.
H. Yasuda et al., "Polymerization of Organic Compounds in an Electroless Glow Discharge. VI. Acetylene with Unusual Co-monomers", J. of Appl. Poly. Sci., 1975, 19, pp. 2845-2858.

* cited by examiner

PACKAGING SOLUTIONS

PRIORITY CLAIM

The present application claims priority to U.S. Provisional Patent Application Ser. No. 63/063,715, entitled "Packaging Solutions," filed Aug. 10, 2020, and incorporated by reference herein in its entirety.

BACKGROUND

The present disclosure generally relates to packaging solutions for ophthalmic devices such as contact lenses.

Ophthalmic devices such as ophthalmic lenses made from, for example, silicone-containing materials, have been investigated for a number of years. Such materials can generally be subdivided into two major classes, namely, hydrogels and non-hydrogels. Hydrogels can absorb and retain water in an equilibrium state, whereas non-hydrogels do not absorb appreciable amounts of water. Regardless of their water content, both hydrogel and non-hydrogel silicone medical devices tend to have relatively hydrophobic, non-wettable surfaces that have a high affinity for lipids. This problem is of particular concern with contact lenses.

Those skilled in the art have long recognized the need for modifying the surface of contact lenses so that they are compatible with the eye. It is known that increased hydrophilicity of the lens surface improves the wettability of the contact lens. This, in turn, is associated with improved wear comfort of contact lenses. Additionally, the surface of the lens can affect the lens's susceptibility to deposition, particularly the deposition of proteins and lipids resulting from tear fluid during lens wear. Accumulated deposition can cause eye discomfort or even inflammation. In the case of extended wear lenses (i.e., lenses used without daily removal of the lens before sleep), the surface is especially important, since extended wear lenses must be designed for high standards of comfort and biocompatibility over an extended period of time.

One approach to enhance wettability of the lens is to carry out a surface post treatment step of the lens. However, the additional step(s) required added cost and time to the manufacturing process.

Blister-packs and glass vials are typically used to individually package each soft contact lens for sale to a customer. Saline or deionized water is commonly used to store the lens in the blister-packs, as mentioned in various patents related to the packaging or manufacturing of contact lenses. Because lens material may tend to stick to itself and to the lens package, packaging solutions for blister-packs have sometimes been formulated to reduce or eliminate lens folding and sticking.

Accordingly, it would be desirable to provide an improved packaging system for ophthalmic devices such as a contact lens such that the lens would be comfortable to wear in actual use and allow for extended wear of the lens without irritation or other adverse effects to the cornea.

SUMMARY

In accordance with one illustrative embodiment, a packaging system for the storage of an ophthalmic device is provided comprising a sealed container containing one or more unused ophthalmic devices immersed in an aqueous packaging solution comprising (a) one or more osmoprotectants, (b) one or more poloxamer comfort agents and (c) one or more polyol demulcents, wherein the aqueous packaging solution has an osmolality of at least about 150 mOsm/kg, a pH of about 6 to about 9 and is heat sterilized.

In accordance with a second illustrative embodiment, a method of preparing a package comprising a storable, sterile ophthalmic device is provided, the method comprising: (a) providing an ophthalmic device; (b) immersing the ophthalmic device in an aqueous packaging solution comprising (i) one or more osmoprotectants, (ii) one or more poloxamer comfort agents and (iii) one or more polyol demulcents, wherein the aqueous packaging solution has an osmolality of at least about 150 mOsm/kg and a pH in the range of about 6 to about 9; (c) packaging the aqueous packaging solution and the ophthalmic device in a manner preventing contamination of the ophthalmic device by microorganisms; and (d) sterilizing the packaged solution and ophthalmic device.

The aqueous packaging solutions described herein containing (a) one or more osmoprotectants, (b) one or more poloxamer comfort agents and (c) one or more polyol demulcents are believed to provide a more uniform coating on the surface of an ophthalmic device such as a contact lens thereby resulting in improved lubricity and/or wettability of the lens. Thus, the lens will be more comfortable to wear in actual use and allow for extended wear of the lens without irritation or other adverse effects to the cornea. Hydrophilic and/or lubricious surfaces of the ophthalmic devices herein such as contact lenses substantially prevent or limit the adsorption of tear lipids and proteins on, and their eventual absorption into, the lenses, thus preserving the clarity of the contact lenses. This, in turn, preserves their performance quality thereby providing a higher level of comfort to the wearer.

DETAILED DESCRIPTION

Exemplary embodiments will now be discussed in further detail with regard to a packaging system for the storage of ophthalmic devices intended for direct contact with body tissue or body fluid. As used herein, the term "ophthalmic device" refers to devices that reside in or on the eye. These lenses can provide optical correction, wound care, drug delivery, diagnostic functionality or cosmetic enhancement or effect or a combination of these properties. Representative examples of such devices include, but are not limited to, soft contact lenses, e.g., a soft, hydrogel lens; soft, non-hydrogel lens and the like, hard contact lenses, e.g., a hard, gas permeable lens material and the like, intraocular lenses, overlay lenses, ocular inserts, optical inserts and the like. As is understood by one skilled in the art, a lens is considered to be "soft" if it can be folded back upon itself without breaking. Any material known to produce an ophthalmic device including a contact lens can be used herein.

The ophthalmic devices can be any material known in the art capable of forming an ophthalmic device as described above. In one embodiment, an ophthalmic device includes devices which are formed from material not hydrophilic per se. Such devices are formed from materials known in the art and include, by way of example, polysiloxanes, perfluoropolyethers, fluorinated poly(meth)acrylates or equivalent fluorinated polymers derived, e.g., from other polymerizable carboxylic acids, polyalkyl(meth)acrylates or equivalent alkylester polymers derived from other polymerizable carboxylic acids, or fluorinated polyolefins, such as fluorinated ethylene propylene polymers, or tetrafluoroethylene, preferably in combination with a dioxol, e.g., perfluoro-2,2-dimethyl-1,3-dioxol. Representative examples of suitable bulk materials include, but are not limited to, lotrafilcon A, neofocon, pasifocon, telefocon, silafocon, fluorsilfocon, paflufocon, silafocon, elastofilcon, fluorofocon or Teflon AF materials, such as Teflon AF 1600 or Teflon AF 2400 which are copolymers of about 63 to about 73 mol % of perfluoro-2,2-dimethyl-1,3-dioxol and about 37 to about 27 mol % of tetrafluoroethylene, or of about 80 to about 90 mol % of perfluoro-2,2-dimethyl-1,3-dioxol and about 20 to about 10 mol % of tetrafluoroethylene.

In another illustrative embodiment, an ophthalmic device includes a device which is formed from material hydrophilic per se, since reactive groups, e.g., carboxy, carbamoyl, sulfate, sulfonate, phosphate, amine, ammonium or hydroxy groups, are inherently present in the material and therefore also at the surface of an ophthalmic device manufactured therefrom. Such devices are formed from materials known in the art and include, by way of example, polyhydroxyethyl acrylate, polyhydroxyethyl methacrylate (HEMA), polyvinyl pyrrolidone (PVP), polyacrylic acid, polymethacrylic acid, polyacrylamide, polydimethylacrylamide (DMA), polyvinyl alcohol and the like and copolymers thereof, e.g., from two or more monomers selected from hydroxyethyl acrylate, hydroxyethyl methacrylate, N-vinyl pyrrolidone, acrylic acid, methacrylic acid, acrylamide, dimethyl acrylamide, vinyl alcohol and the like. Representative examples of suitable bulk materials include, but are not limited to, polymacon, tefilcon, methafilcon, deltafilcon, bufilcon, phemfilcon, ocufilcon, focofilcon, etafilcon, hefilcon, vifilcon, tetrafilcon, perfilcon, droxifilcon, dimefilcon, isofilcon, mafilcon, nelfilcon, atlafilcon and the like. Examples of other suitable bulk materials include balafilcon A, hilafilcon A, alphafilcon A, bilafilcon B and the like.

In another illustrative embodiment, an ophthalmic device includes a device which is formed from materials which are amphiphilic segmented copolymers containing at least one hydrophobic segment and at least one hydrophilic segment which are linked through a bond or a bridge member.

It is particularly useful to employ biocompatible materials herein including both soft and rigid materials commonly used for ophthalmic lenses, including contact lenses. In general, non-hydrogel materials are hydrophobic polymeric materials that do not contain water in their equilibrium state. Typical non-hydrogel materials comprise silicone acrylics, such as those formed from a bulky silicone monomer (e.g., tris(trimethylsiloxy)silylpropyl methacrylate, commonly known as "TRIS" monomer), methacrylate end-capped poly (dimethylsiloxane)prepolymer, or silicones having fluoroalkyl side groups (polysiloxanes are also commonly known as silicone polymers).

Hydrogels in general are a well-known class of materials that comprise hydrated, crosslinked polymeric systems containing water in an equilibrium state. Accordingly, hydrogels are copolymers prepared from hydrophilic monomers. In the case of silicone hydrogels, the hydrogel copolymers are generally prepared by polymerizing a mixture containing at least one device-forming silicone-containing monomer and at least one device-forming hydrophilic monomer. Either the silicone-containing monomer or the hydrophilic monomer can function as a crosslinking agent (a crosslinker being defined as a monomer having multiple polymerizable functionalities) or a separate crosslinker may be employed. Silicone hydrogels typically have a water content between about 10 to about 80 weight percent.

Representative examples of useful hydrophilic monomers include, but are not limited to, amides such as N,N-dimethylacrylamide and N,N-dimethylmethacrylamide; cyclic lactams such as N-vinyl-2-pyrrolidone; and (meth)acrylated poly(alkene glycols), such as poly(diethylene glycols) of varying chain length containing monomethacrylate or dimethacrylate end caps. Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277, the disclosures of which are incorporated herein by reference. Other suitable hydrophilic monomers will be apparent to one skilled in the art. For example, 2-hydroxyethylmethacrylate (HEMA) is a well-known hydrophilic monomer that may be used in admixture with the aforementioned hydrophilic monomers.

The monomer mixtures may also include a second device-forming monomer including a copolymerizable group and a reactive functional group. The copolyermizable group is preferably an ethylenically unsaturated group, such that this device-forming monomer copolymerizes with the hydrophilic device-forming monomer and any other device-forming monomers in the initial device-forming monomer mixture. Additionally, the second monomer can include a reactive functional group that reacts with a complementary reactive group of the copolymer which is the reaction product of one or more polymerizable polyhydric alcohols and one or more polymerizable fluorine-containing monomers. In other words, after the device is formed by copolymerizing the device-forming monomer mixture, the reactive functional groups provided by the second device-forming monomers remain to react with a complementary reactive moiety of the copolymer.

In one illustrative embodiment, reactive groups of the second device-forming monomers include epoxide groups. Accordingly, second device-forming monomers are those that include both an ethylenically unsaturated group (that permits the monomer to copolymerize with the hydrophilic device-forming monomer) and the epoxide group (that does not react with the hydrophilic device-forming monomer but remains to react with the copolymer is the reaction product of one or more polymerizable polyhydric alcohols and one or more polymerizable fluorine-containing monomers). Examples include glycidyl methacrylate, glycidyl acrylate, glycidyl vinylcarbonate, glycidyl vinylcarbamate, 4-vinyl-1-cyclohexene-1,2-epoxide and the like.

As mentioned, one class of ophthalmic device substrate materials are silicone hydrogels. In this case, the initial device-forming monomer mixture further comprises a silicone-containing monomer. Applicable silicone-containing monomeric materials for use in the formation of silicone hydrogels are well known in the art and numerous examples are provided in U.S. Pat. Nos. 4,136,250; 4,153,641; 4,740, 533; 5,034,461; 5,070,215; 5,260,000; 5,310,779; and 5,358,995. Specific examples of suitable materials for use herein include those disclosed in U.S. Pat. Nos. 5,310,779; 5,387,662; 5,449,729; 5,512,205; 5,610,252; 5,616,757; 5,708,094; 5,710,302; 5,714,557 and 5,908,906, the contents of which are incorporated by reference herein.

Representative examples of applicable silicon-containing monomers include bulky polysiloxanylalkyl(meth)acrylic monomers. An example of a bulky polysiloxanylalkyl(meth) acrylic monomer is represented by the structure of Formula I:

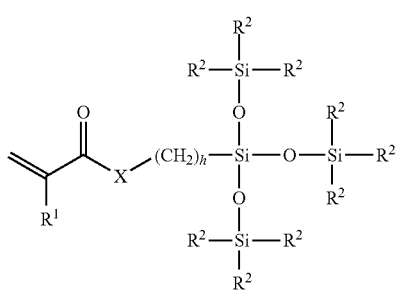

(I)

wherein X denotes —O— or —NR— wherein R denotes hydrogen or a $C_1$ to $C_4$ alkyl; each $R^1$ independently denotes hydrogen or methyl; each $R^2$ independently denotes a lower alkyl radical, a phenyl radical or a group represented by

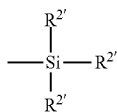

wherein each $R^{2'}$ independently denotes a lower alkyl radical or a phenyl radical; and h is 1 to 10.

Examples of bulky monomers are methacryloxypropyl tris(trimethyl-siloxy)silane or tris(trimethylsiloxy)silylpropyl methacrylate, sometimes referred to as TRIS and tris(trimethylsiloxy)silylpropyl vinyl carbamate, sometimes referred to as TRIS-VC and the like.

Such bulky monomers may be copolymerized with a silicone macromonomer, which is a poly(organosiloxane) capped with an unsaturated group at two or more ends of the molecule. U.S. Pat. No. 4,153,641 discloses, for example, various unsaturated groups such as acryloxy or methacryloxy groups.

Another class of representative silicone-containing monomers includes, for example, silicone-containing vinyl carbonate or vinyl carbamate monomers such as, for example, 1,3-bis[4-vinyloxycarbonyloxy)but-1-yl]tetramethyl-disiloxane; 3-(trimethylsilyl)propyl vinyl carbonate; 3-(vinyloxycarbonylthio)propyl-[tris(trimethylsiloxy)silane]; 3-[tris(trimethylsiloxy)silyl]propyl vinyl carbamate; 3-[tris(trimethylsiloxy)silyl]propyl allyl carbamate; 3-[tris(trimethylsiloxy)silyl]propyl vinyl carbonate; t-butyldimethylsiloxyethyl vinyl carbonate; trimethylsilylethyl vinyl carbonate; trimethylsilylmethyl vinyl carbonate and the like and mixtures thereof.

Another class of silicon-containing monomers includes polyurethane-polysiloxane macromonomers (also sometimes referred to as prepolymers), which may have hard-soft-hard blocks like traditional urethane elastomers. They may be end-capped with a hydrophilic monomer such as HEMA. Examples of such silicone urethanes are disclosed in a variety or publications, including Lai, Yu-Chin, "The Role of Bulky Polysiloxanylalkyl Methacryates in Polyurethane-Polysiloxane Hydrogels," Journal of Applied Polymer Science, Vol. 60, 1193-1199 (1996). PCT Published Application No. WO 96/31792 discloses examples of such monomers, which disclosure is hereby incorporated by reference in its entirety. Further examples of silicone urethane monomers are represented by Formulae II and III:

$$E(*D*A*D*G)_a*D*A*D*E'; \text{ or} \tag{II}$$

$$E(*D*G*D*A)_a*D*A*D*E'; \text{ or} \tag{III}$$

wherein:

D independently denotes an alkyl diradical, an alkyl cycloalkyl diradical, a cycloalkyl diradical, an aryl diradical or an alkylaryl diradical having 6 to about 30 carbon atoms;

G independently denotes an alkyl diradical, a cycloalkyl diradical, an alkyl cycloalkyl diradical, an aryl diradical or an alkylaryl diradical having 1 to about 40 carbon atoms and which may contain ether, thio or amine linkages in the main chain;

\* denotes a urethane or ureido linkage;

a is at least 1;

A independently denotes a divalent polymeric radical of Formula IV:

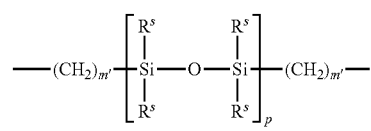

(IV)

wherein each $R^s$ independently denotes an alkyl or fluoro-substituted alkyl group having 1 to about 10 carbon atoms which may contain ether linkages between the carbon atoms; m' is at least 1; and p is a number that provides a moiety weight of about 400 to about 10,000;

each of E and E' independently denotes a polymerizable unsaturated organic radical represented by Formula V:

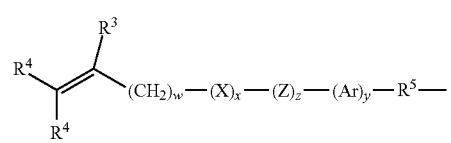

(V)

wherein: $R^3$ is hydrogen or methyl;

$R^4$ is hydrogen, an alkyl radical having 1 to 6 carbon atoms, or a —CO—Y—$R^6$ radical wherein Y is —O—, —S— or —NH—;

$R^5$ is a divalent alkylene radical having 1 to about 10 carbon atoms;

$R^6$ is a alkyl radical having 1 to about 12 carbon atoms;

X denotes —CO— or —OCO—;

Z denotes —O— or —NH—;

Ar denotes an aromatic radical having about 6 to about 30 carbon atoms;

w is 0 to 6; x is 0 or 1; y is 0 or 1; and z is 0 or 1.

In one illustrative embodiment, a silicone-containing urethane monomer is represented by Formula VI:

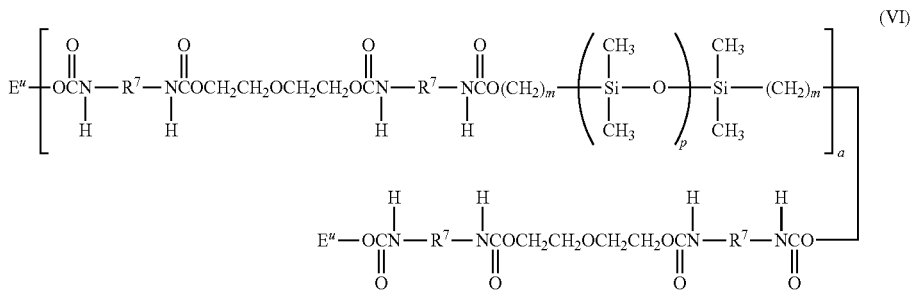

(VI)

wherein m is at least 1 and is preferably 3 or 4, a is at least 1 and preferably is 1, p is a number which provides a moiety weight of about 400 to about 10,000 and is preferably at least about 30, $R^7$ is a diradical of a diisocyanate after removal of the isocyanate group, such as the diradical of isophorone diisocyanate, and each E" is a group represented by:

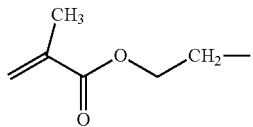

In another embodiment, a silicone hydrogel material comprises (in bulk, that is, in the monomer mixture that is copolymerized) about 5 to about 50 percent, or from about 10 to about 25 percent, by weight of one or more silicone macromonomers, about 5 to about 75 percent, or about 30 to about 60 percent, by weight of one or more polysiloxanyl-alkyl (meth)acrylic monomers, and about 10 to about 50 percent, or about 20 to about 40 percent, by weight of a hydrophilic monomer. In general, the silicone macromonomer is a poly(organosiloxane) capped with an unsaturated group at two or more ends of the molecule. In addition to the end groups in the above structural formulas, U.S. Pat. No. 4,153,641 discloses additional unsaturated groups, including acryloxy or methacryloxy. Fumarate-containing materials such as those disclosed in U.S. Pat. Nos. 5,310,779; 5,449,729 and 5,512,205 are also useful substrates in accordance with the illustrative non-limiting embodiments described herein. The silane macromonomer may be a silicon-containing vinyl carbonate or vinyl carbamate or a polyurethane-polysiloxane having one or more hard-soft-hard blocks and end-capped with a hydrophilic monomer.

Another class of representative silicone-containing monomers includes fluorinated monomers. Such monomers have been used in the formation of fluorosilicone hydrogels to reduce the accumulation of deposits on contact lenses made therefrom, as disclosed in, for example, U.S. Pat. Nos. 4,954,587; 5,010,141 and 5,079,319. Also, the use of silicone-containing monomers having certain fluorinated side groups, i.e., —($CF_2$)—H, have been found to improve compatibility between the hydrophilic and silicone-containing monomeric units. See, e.g., U.S. Pat. Nos. 5,321,108 and 5,387,662.

The above silicone materials are merely exemplary, and other materials for use as substrates according to those described herein that have been disclosed in various publications and are being continuously developed for use in contact lenses and other medical devices can also be used. For example, an ophthalmic device can be formed from at least a cationic monomer such as cationic silicone-containing monomer or cationic fluorinated silicone-containing monomers.

Contact lenses for application in the illustrative embodiments described herein can be manufactured employing various conventional techniques, to yield a shaped article having the desired posterior and anterior lens surfaces. For example, spincasting methods are disclosed in U.S. Pat. Nos. 3,408,429 and 3,660,545; and static casting methods are disclosed in U.S. Pat. Nos. 4,113,224, 4,197,266 and 5,271,876. Curing of the monomeric mixture may be followed by a machining operation in order to provide a contact lens having a desired final configuration. As an example, U.S. Pat. No. 4,555,732 discloses a process in which an excess of a monomeric mixture is cured by spincasting in a mold to form a shaped article having an anterior lens surface and a relatively large thickness. The posterior surface of the cured spincast article is subsequently lathe cut to provide a contact lens having the desired thickness and posterior lens surface. Further machining operations may follow the lathe cutting of the lens surface, for example, edge-finishing operations.

Typically, an organic diluent is included in the initial monomeric mixture in order to minimize phase separation of polymerized products produced by polymerization of the monomeric mixture and to lower the glass transition temperature of the reacting polymeric mixture, which allows for a more efficient curing process and ultimately results in a more uniformly polymerized product. Sufficient uniformity of the initial monomeric mixture and the polymerized product is of particular importance for silicone hydrogels, primarily due to the inclusion of silicone-containing monomers which may tend to separate from the hydrophilic comonomer.

Suitable organic diluents include, for example, monohydric alcohols such as $C_6$ to $C_{10}$ straight-chained aliphatic monohydric alcohols, e.g., n-hexanol and n-nonanol; diols such as ethylene glycol; polyols such as glycerin; ethers such as diethylene glycol monoethyl ether; ketones such as methyl ethyl ketone; esters such as methyl enanthate; and hydrocarbons such as toluene. Preferably, the organic diluent is sufficiently volatile to facilitate its removal from a cured article by evaporation at or near ambient pressure.

Generally, the diluent may be included at about 5 to about 60 percent by weight of the monomeric mixture. In one embodiment, the diluent may be included at about 10 to about 50 percent by weight of the monomeric mixture. If necessary, the cured lens may be subjected to solvent removal, which can be accomplished by evaporation at or near ambient pressure or under vacuum. An elevated temperature can be employed to shorten the time necessary to evaporate the diluent.

Following removal of the organic diluent, the lens can then be subjected to mold release and optional machining operations. The machining step includes, for example, buffing or polishing a lens edge and/or surface. Generally, such machining processes may be performed before or after the article is released from a mold part. As an example, the lens may be dry released from the mold by employing vacuum tweezers to lift the lens from the mold.

As one skilled in the art will readily appreciate, ophthalmic device surface functional groups of the ophthalmic device may be inherently present at the surface of the device. However, if the ophthalmic device contains too few or no functional groups, the surface of the device can be modified by known techniques, for example, plasma chemical methods (see, for example, WO 94/06485), or conventional functionalization with groups such as —OH, —NH$_2$ or —CO$_2$H. Suitable ophthalmic device surface functional groups of the ophthalmic device include a wide variety of groups well known to the skilled artisan. Representative examples of such functional groups include, but are not limited to, hydroxy groups, amino groups, carboxy groups, carbonyl groups, aldehyde groups, sulfonic acid groups, sulfonyl chloride groups, isocyanato groups, carboxy anhydride groups, lactone groups, azlactone groups, epoxy groups and groups being replaceable by amino or hydroxy groups, such as halo groups, or mixtures thereof. In one embodiment, the ophthalmic device surface functional groups of the ophthalmic device are amino groups and/or hydroxy groups.

In one embodiment, the foregoing ophthalmic devices can be subjected to an oxidative surface treatment such as corona discharge or plasma oxidation followed by treatment with the aqueous packaging solution according to the illustrative non-limiting embodiments described herein. For example, an ophthalmic device such as a silicone hydrogel formulation containing hydrophilic polymers, such as poly(N,N-dimethylacrylamide) or poly(N-vinylpyrrolidinone), is subjected to an oxidative surface treatment to form at least silicates on the surface of the lens and then the lens is treated with an aqueous packaging solution according to the illustrative non-limiting embodiments described herein to render a lubricious, stable, highly wettable surface coating. The complexation treatment is advantageously performed under autoclave conditions (sterilization conditions).

The standard process such as a plasma process (also referred to as "electrical glow discharge processes") provides a thin, durable surface upon the ophthalmic device prior to binding the brush copolymer to at least a portion of the surface thereof. Examples of such plasma processes are provided in U.S. Pat. Nos. 4,143,949; 4,312,575; and 5,464,667.

Although plasma processes are generally well known in the art, a brief overview is provided below. Plasma surface treatments involve passing an electrical discharge through a gas at low pressure. The electrical discharge may be at radio frequency (typically 13.56 MHz), although microwave and other frequencies can be used. Electrical discharges produce ultraviolet (UV) radiation, in addition to being absorbed by atoms and molecules in their gas state, resulting in energetic electrons and ions, atoms (ground and excited states), molecules, and radicals. Thus, a plasma is a complex mixture of atoms and molecules in both ground and excited states, which reach a steady state after the discharge is begun. The circulating electrical field causes these excited atoms and molecules to collide with one another as well as the walls of the chamber and the surface of the material being treated.

The deposition of a coating from a plasma onto the surface of a material has been shown to be possible from high-energy plasmas without the assistance of sputtering (sputter-assisted deposition). Monomers can be deposited from the gas phase and polymerized in a low-pressure atmosphere (about 0.005 to about 5 torr, and preferably about 0.001 to about 1 torr) onto a substrate utilizing continuous or pulsed plasmas, suitably as high as about 1000 watts. A modulated plasma, for example, may be applied about 100 milliseconds on then off. In addition, liquid nitrogen cooling has been utilized to condense vapors out of the gas phase onto a substrate and subsequently use the plasma to chemically react these materials with the substrate. However, plasmas do not require the use of external cooling or heating to cause the deposition. Low or high wattage (e.g., about 5 to about 1000 watts, and preferably about 20 to about 500 watts) plasmas can coat even the most chemical-resistant substrates, including silicones.

After initiation by a low energy discharge, collisions between energetic free electrons present in the plasma cause the formation of ions, excited molecules, and free-radicals. Such species, once formed, can react with themselves in the gas phase as well as with further ground-state molecules. The plasma treatment may be understood as an energy dependent process involving energetic gas molecules. For chemical reactions to take place at the surface of the lens, one needs the required species (element or molecule) in terms of charge state and particle energy. Radio frequency plasmas generally produce a distribution of energetic species. Typically, the "particle energy" refers to the average of the so-called Boltzman-style distribution of energy for the energetic species. In a low-density plasma, the electron energy distribution can be related by the ratio of the electric field strength sustaining the plasma to the discharge pressure (E/p). The plasma power density P is a function of the wattage, pressure, flow rates of gases, etc., as will be appreciated by the skilled artisan. Background information on plasma technology, hereby incorporated by reference, includes the following: A. T. Bell, Proc. Intl. Conf Phenom. Ioniz. Gases, "Chemical Reaction in Nonequilibrium Plasmas", 19-33 (1977); J. M. Tibbitt, R. Jensen, A. T. Bell, M. Shen, Macromolecules, "A Model for the Kinetics of Plasma Polymerization", 3, 648-653 (1977); J. M. Tibbitt, M. Shen, A. T. Bell, J. Macromol. Sci.-Chem., "Structural Characterization of Plasma-Polymerized Hydrocarbons", A10, 1623-1648 (1976); C. P. Ho, H. Yasuda, J. Biomed, Mater. Res., "Ultrathin coating of plasma polymer of methane applied on the surface of silicone contact lenses", 22, 919-937 (1988); H. Kobayashi, A. T. Bell, M. Shen, Macromolecules, "Plasma Polymerization of Saturated and Unsaturated Hydrocarbons", 3, 277-283 (1974); R. Y. Chen, U.S. Pat. No. 4,143,949, Mar. 13, 1979, "Process for Putting a Hydrophilic Coating on a Hydrophobic Contact Lens"; and H. Yasuda, H. C. Marsh, M. O. Bumgarner, N. Morosoff, J. of Appl. Poly. Sci., "Polymerization of Organic Compounds in an Electroless Glow Discharge. VI. Acetylene with Unusual Co-monomers", 19, 2845-2858 (1975).

Based on this previous work in the field of plasma technology, the effects of changing pressure and discharge power on the rate of plasma modification can be understood. The rate generally decreases as the pressure is increased. Thus, as pressure increases the value of E/p, the ratio of the electric field strength sustaining the plasma to the gas pressure decreases and causes a decrease in the average electron energy. The decrease in electron energy in turn causes a reduction in the rate coefficient of all electron-molecule collision processes. A further consequence of an increase in pressure is a decrease in electron density. Providing that the pressure is held constant, there should be a linear relationship between electron density and power.

In practice, contact lenses are surface-treated by placing them, in their unhydrated state, within an electric glow discharge reaction vessel (e.g., a vacuum chamber). Such reaction vessels are commercially available. The lenses may be supported within the vessel on an aluminum tray (which acts as an electrode) or with other support devices designed to adjust the position of the lenses. The use of a specialized support devices which permit the surface treatment of both sides of a lens are known in the art and may be used herein.

As mentioned above, the surface of the lens, for example, a silicone hydrogel continuous-wear lens is initially treated, e.g., oxidized, by the use of a plasma to render the subsequent brush copolymer surface deposition more adherent to the lens. Such a plasma treatment of the lens may be accomplished in an atmosphere composed of a suitable media, e.g., an oxidizing media such as oxygen, air, water, peroxide, $O_2$ (oxygen gas), etc., or appropriate combinations thereof, typically at an electric discharge frequency of about 13.56 Mhz, or between about 20 to about 500 watts at a pressure of about 0.1 to about 1.0 torr, or for about 10 seconds to about 10 minutes or more, or about 1 to about 10 minutes. It is preferred that a relatively "strong" plasma is utilized in this step, for example, ambient air drawn through a five percent (5%) hydrogen peroxide solution. Those skilled in the art will know other methods of improving or promoting adhesion for bonding of the subsequent brush copolymer layer.

Next, the ophthalmic device such as a contact lens will be immersed in an aqueous packaging solution and stored in a packaging system according to non-limiting illustrative embodiments described herein. Generally, a packaging system for the storage of an ophthalmic device includes at least a sealed container containing one or more unused ophthalmic devices immersed in an aqueous packaging solution. In one embodiment, the sealed container is a hermetically sealed blister-pack, in which a concave well containing an ophthalmic device such as a contact lens is covered by a metal or plastic sheet adapted for peeling in order to open the blister-pack. The sealed container may be any suitable generally inert packaging material providing a reasonable degree of protection to the lens, preferably a plastic material such as polyalkylene, PVC, polyamide, and the like.

In one illustrative non-limiting embodiment, an aqueous packaging solution will contain at least (a) one or more osmoprotectants, (b) one or more poloxamer comfort agents and (c) one or more demulcent polyols. Suitable osmoprotectants include, for example, polyols, amino acids and methylamine-containing compounds. Suitable polyols for use herein can have the formula $R''(OH)_y$ where $R''$ is a hydrocarbon radical and y is an integer representing the number of hydroxy radicals and has a value of, for example, from 3 to about 12, or from 4 to about 8. The polyols may contain less than about 12 carbon atoms such as from 4 to about 12 carbon atoms. Examples of suitable polyols include, but are not limited to, alkylene glycols and poly(oxyalkylene) glycols, e.g., ethylene glycol, di(ethylene glycol), tri(ethylene glycol), di(propylene glycol), tri(butylene glycol), penta(ethylene glycol), and other poly(oxyalkylene) glycols formed by the condensation of two or more moles of ethylene glycol, propylene glycol, octylene glycol, or a like glycol having up to 12 carbon atoms in the alkylene radical. Other examples of suitable polyols include, but are not limited to, pentaerythritol, erythritol, sucrose, trehalose, xylitol, raffinose, raffinose/galactinol and the like. In one embodiment, a polyol is erythritol.

Suitable amino acids include, for example, amino acids occurring in the natural collagen of the cornea, such as betaine, glycine betaine, glycine, diglycine, proline, glutamine, alanine, arganine, asparagine, lysine, leucine, serine and isoleucine.

Suitable methylamine-containing compounds include, for example, sarcosine, trimethylamine N-oxide, betaine, glycine betaine and L-carnitine.

The amount of the one or more osmoprotectants employed in a packaging solution for storing an ophthalmic device in a packaging system is an amount effective to improve the surface properties of the ophthalmic device. It is believed these osmoprotectants enhance initial and extended comfort when a contact lens, packaged in the solution and then removed from the packaging system, is placed on the eye for wearing. In one embodiment, the concentration of the one or more osmoprotectants present in the aqueous packaging solution will range from about 0.01% to about 10% w/w. In one embodiment, the concentration of the one or more osmoprotectants present in the aqueous packaging solution will range from about 0.1% to about 10% w/w. In one embodiment, the concentration of the one or more osmoprotectants present in the aqueous packaging solution will range from about 0.01 wt. % to about 5.0 wt. %, based on the total weight of the aqueous packaging solution, of the one or more osmoprotectants.

The aqueous packaging solution will further contain one or more poloxamer comfort agents. A representative example of a suitable poloxamer comfort agent is a poloxamer block copolymer. One specific class of poloxamer block copolymers are those available under the trademark Pluronic (BASF Wyandotte Corp., Wyandotte, Mich.). Poloxamers include Pluronics and reverse Pluronics. Pluronics are a series of ABA block copolymers composed of poly(ethylene oxide)-poly(propylene oxide)-poly(ethylene oxide) blocks as generally represented in Formula VII:

$$HO(C_2H_4O)_a(C_3H_6O)_b(C_2H_4O)_aH \qquad (VII)$$

wherein a is independently at least 1 and b is at least 1.

Reverse Pluronics are a series of BAB block copolymers, respectively composed of poly(propylene oxide)-poly(ethylene oxide)-poly(propylene oxide) blocks as generally represented in Formula VIII:

$$HO(C_3H_6O)_b(C_2H_4O)_a(C_3H_6O)_bH \qquad (VIII)$$

wherein a is at least 1 and b is independently at least 1.

The poly(ethylene oxide), PEO, blocks are hydrophilic, whereas the poly(propylene oxide), PPO, blocks are hydrophobic in nature. The poloxamers in each series have varying ratios of PEO and PPO which ultimately determines the hydrophilic-lipophilic balance (HLB) of the material, i.e., the varying HLB values are based upon the varying values of a and b, a representing the number of hydrophilic poly(ethylene oxide) units (PEO) being present in the molecule and b representing the number of hydrophobic poly(propylene oxide) units (PPO) being present in the molecule. In one embodiment, the poloxamer will have an HLB ranging from about 5 to about 24. In one embodiment, the poloxamer will have an HLB ranging from about 1 to about 5.

The average number of units of polyoxyethylene and polyoxypropylene varies based on the number associated with the polymer. For example, the smallest polymer, Poloxamer 101, consists of a block with an average of 2 units of polyoxyethylene, a block with an average of 16 units of polyoxypropylene, followed by a block with an average of 2 units of polyoxyethylene. Examples of poloxamers include, but are not limited to, Poloxamer 101, Poloxamer 105, Poloxamer 108, Poloxamer 122, Poloxamer 123, Poloxamer 124, Poloxamer 181, Poloxamer 182, Poloxamer 183, Poloxamer 184, Poloxamer 185, Poloxamer 188, Poloxamer 212, Poloxamer 215, Poloxamer 217, Poloxamer 231, Poloxamer 234, Poloxamer 235, Poloxamer 237, Poloxamer 238, Poloxamer 282, Poloxamer 284, Poloxamer 288, Poloxamer 331, Poloxamer 333, Poloxamer 334, Poloxamer 335, Poloxamer 338, Poloxamer 401, Poloxamer 402, Poloxamer 403 and Poloxamer 407.

Poloxamers and reverse poloxamers have terminal hydroxyl groups that can be terminal functionalized. An example of a terminal functionalized poloxamer and as discussed herein is poloxamer dimethacrylate (e.g., Pluronic® F127 dimethacrylate) as disclosed in U.S. Patent Application Publication No. 2003/0044468 and U.S. Pat. No. 9,309,357. Other examples include glycidyl-terminated copolymers of polyethylene glycol and polypropylene glycol as disclosed in U.S. Pat. No. 6,517,933.

The poloxamer is functionalized to provide the desired reactivity at the end terminal of the molecule. The functionality can be varied and is determined based upon the intended use of the functionalized PEO- and PPO-containing block copolymers. That is, the PEO- and PPO-containing block copolymers are reacted to provide end terminal functionality that is complementary with the intended device forming monomeric mixture. The term block copolymer as used herein shall be understood to mean a poloxamer as having two or more blocks in their polymeric backbone(s).

In one embodiment, the one or more poloxamer comfort agents are present in the aqueous packaging solution in an amount ranging from about 0.001 to about 5.0 wt. %, based on the total weight of the aqueous packaging solution. In another illustrative embodiment, the one or more poloxamer comfort agents are present in the aqueous packaging solution in an amount ranging from about 0.01 to about 1.0 wt. %, based on the total weight of the aqueous packaging solution.

The aqueous packaging solution will further contain one or more polyol demulcents. Suitable polyols for use herein have the formula R"(OH)$_y$, where R" is a hydrocarbon radical and y is an integer representing the number of hydroxy radicals and has a value of from 2 to 3. The polyols may contain less than about 12 carbon atoms such as from 3 to about 12 carbon atoms. Representative examples of polyol demulcents include glycerol, propylene glycol, polyethylene glycol 300, polyethylene glycol 400, and polysorbate 80. As one skilled in the art will readily appreciate, the one or more polyol demulcents will be different than a polyol osmoprotectant.

In one embodiment, the one or more polyol demulcents are present in the aqueous packaging solution in an amount ranging from about 0.01 to about 10.0 wt. %, based on the total weight of the aqueous packaging solution. In another illustrative embodiment, the one or more polyol demulcents are present in the aqueous packaging solution in an amount ranging from about 0.1 wt. % to about 3.0 wt. %, based on the total weight of the aqueous packaging solution. In another illustrative embodiment, the one or more polyol demulcents are present in the aqueous packaging solution in an amount ranging from about 0.1 to about 2.0 wt. %, based on the total weight of the aqueous packaging solution.

The aqueous packaging solution may further contain one or more poloxamines. While the poloxamers and reverse poloxamers are considered to be difunctional molecules (based on the terminal hydroxyl groups), the poloxamines are in a tetrafunctional form, i.e., the molecules are tetrafunctional block copolymers terminating in primary hydroxyl groups and linked by a central diamine. One specific class of poloxamine block copolymers are those available under the trademark Tetronic (BASF). Poloxamines include Tetronic and reverse Tetronics. Poloxamines have the following general structure of Formula IX:

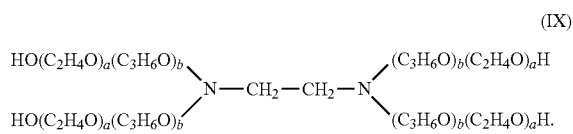

(IX)

wherein a is independently at least 1 and b is independently at least 1.

The poloxamine is functionalized to provide the desired reactivity at the end terminal of the molecule. The functionality can be varied and is determined based upon the intended use of the functionalized PEO- and PPO-containing block copolymers. That is, the PEO- and PPO-containing block copolymers are reacted to provide end terminal functionality that is complementary with the intended device forming monomeric mixture. The term block copolymer as used herein shall be understood to mean a poloxamine as having two or more blocks in their polymeric backbone(s).

In one embodiment, the one or more poloxamines are present in the aqueous packaging solution in an amount ranging from about 0.001 to about 5.0 wt. %, based on the total weight of the aqueous packaging solution. In another illustrative embodiment, the one or more poloxamines are present in the aqueous packaging solution in an amount ranging from about 0.1 to about 1.2 wt. %, based on the total weight of the aqueous packaging solution.

The aqueous packaging solutions according to illustrative embodiments described herein are physiologically compatible. Specifically, the aqueous packaging solutions must be "ophthalmically safe" for use with a contact lens, meaning that a contact lens treated with the solution is generally suitable and safe for direct placement on the eye without rinsing, that is, the solution is safe and comfortable for daily contact with the eye via a contact lens that has been wetted with the solution. An ophthalmically safe solution has a tonicity and pH that is compatible with the eye and includes materials, and amounts thereof, that are non-cytotoxic according to ISO standards and U.S. Food & Drug Administration (FDA) regulations.

The aqueous packaging solution should also be sterile in that the absence of microbial contaminants in the product prior to release must be statistically demonstrated to the degree necessary for such products. The liquid media useful herein are selected to have no substantial detrimental effect on the lens being treated or cared for and to allow or even facilitate the present lens treatment or treatments. In one embodiment, the liquid media is aqueous-based. A particularly useful aqueous liquid medium is that derived from saline, for example, a conventional saline solution or a conventional buffered saline solution.

The pH of the aqueous packaging solutions should be maintained within the range of about 6 to about 9, or from about 6.5 to about 7.8. Suitable buffers may be added, such as boric acid, sodium borate, potassium citrate, citric acid, sodium bicarbonate, TRIS and various mixed phosphate buffers (including combinations of $Na_2HPO_4$, $NaH_2PO_4$ and KH$_2$PO$_4$) and mixtures thereof. Generally, buffers will be used in amounts ranging from about 0.05 to about 2.5 percent by weight of the solution. In one embodiment, buffers will be used in amounts ranging from about 0.1 to about 1.5 percent by weight of the solution. In one embodiment, the aqueous packaging solutions described herein can contain a borate buffer, such as one or more of boric acid, sodium borate, potassium tetraborate and potassium metaborate. In another embodiment, the aqueous packaging solutions described herein can contain a phosphate buffer, such as one or more of sodium phosphate monobasic monohydrate and sodium phosphate dibasic anhydrous.

Typically, the aqueous packaging solutions are also adjusted with tonicity agents, to approximate the osmotic pressure of normal lacrimal fluids which is equivalent to a 0.9 percent solution of sodium chloride or 2.5 percent of glycerol solution. The aqueous packaging solutions are made substantially isotonic with physiological saline used alone or in combination, otherwise if simply blended with sterile water and made hypotonic or made hypertonic the lenses will lose their desirable optical parameters. Correspondingly, excess saline may result in the formation of a hypertonic solution which will cause stinging and eye irritation.

Suitable tonicity adjusting agents include, for example, sodium and potassium chloride, dextrose, calcium and magnesium chloride and the like and mixtures thereof. These tonicity adjusting agents are typically used individually in amounts ranging from about 0.01 to about 2.5% w/v. In one embodiment, the tonicity adjusting agents are used in amounts ranging from about 0.2 to about 1.5% w/v. The tonicity agent will be employed in an amount to provide a final effective osmotic value of at least about 150 mOsm/kg. In one embodiment, the tonicity adjusting agents are used in an amount to provide a final effective osmotic value of from about 150 to about 400 mOsm/kg. In one embodiment, the tonicity adjusting agents are used in an amount to provide a final effective osmotic value of from about 150 to about 350 mOsm/kg. In one embodiment, the tonicity adjusting agents are used in an amount to provide a final effective osmotic value of from about 160 to about 220 mOsm/kg.

If desired, one or more additional components can be included in the packaging solution. Such an additional component or additional components are chosen to impart or provide at least one beneficial or desired property to the packaging solution. In general, the additional components may be selected from components which are conventionally used in one or more ophthalmic device care compositions. Suitable additional components include, for example, cleaning agents, wetting agents, nutrient agents, sequestering agents, viscosity builders, contact lens conditioning agents, antioxidants, and the like and mixtures thereof. These additional components may each be included in the packaging solutions in an amount effective to impart or provide the beneficial or desired property to the packaging solutions. For example, such additional components may be included in the packaging solutions in amounts similar to the amounts of such components used in other, e.g., conventional, contact lens care products.

Suitable sequestering agents include, for example, disodium ethylene diamine tetraacetate, alkali metal hexametaphosphate, citric acid, sodium citrate and the like and mixtures thereof.

Suitable viscosity builders include, for example, hydroxyethyl cellulose, hydroxymethyl cellulose, polyvinyl pyrrolidone, polyvinyl alcohol and the like and mixtures thereof.

Suitable antioxidants include, for example, sodium metabisulfite, sodium thiosulfate, N-acetylcysteine, butylated hydroxyanisole, butylated hydroxytoluene and the like and mixtures thereof.

The method of packaging and storing an ophthalmic device such as a contact lens according to the illustrative embodiments described herein includes at least packaging an ophthalmic device immersed in the aqueous packaging solution described above. The method may include immersing the ophthalmic device in an aqueous packaging solution prior to delivery to the customer/wearer, directly following manufacture of the contact lens. Alternately, the packaging and storing in the packaging solution may occur at an intermediate point before delivery to the ultimate customer (wearer) but following manufacture and transportation of the lens in a dry state, wherein the dry lens is hydrated by immersing the lens in the packaging solution. Consequently, a package for delivery to a customer may include a sealed container containing one or more unused contact lenses immersed in an aqueous packaging solution according to the illustrative non-limiting embodiments described herein.

In one embodiment, the steps leading to the present ophthalmic device packaging system includes (1) molding an ophthalmic device in a mold comprising at least a first and second mold portion, (2) hydrating and cleaning the device in a container comprising at least one of the mold portions, (3) introducing the packaging solution with the copolymer into the container with the device supported therein, and (4) sealing the container. In one embodiment, the method also includes the step of sterilizing the contents of the container. Sterilization may take place prior to, or most conveniently after, sealing of the container and may be affected by any suitable method known in the art, e.g., by autoclaving of the sealed container at temperatures of about 12° C. or higher.

The following examples are merely illustrative and should not be read as limiting the scope of the illustrative non-limiting embodiments described herein as defined in the claims.

Example 1

An aqueous packaging solution was made by mixing the following components, listed in Table 1 at amounts per weight.

TABLE 1

| Ingredient | % w/w |
| --- | --- |
| Sodium Phosphate Monobasic Monohydrate | 0.00925 |
| Sodium Phosphate Dibasic Anhydrous | 0.0320 |
| Potassium Chloride | 0.70 |
| Poloxamine 1107 | 0.550 |
| Poloxamer 181 | 0.020 |
| Glycerol | 0.90 |
| Erythritol | 0.90 |
| Purified Water | Q.S. to 100% w/w |

Example 2

An aqueous packaging solution was made by mixing the following components, listed in Table 2 at amounts per weight.

TABLE 2

| Ingredient | % w/w |
|---|---|
| Sodium Phosphate Monobasic Monohydrate | 0.00925 |
| Sodium Phosphate Dibasic Anhydrous | 0.0320 |
| Potassium Chloride | 0.60 |
| Sodium chloride | 0.20 |
| Poloxamine 1107 | 0.550 |
| Poloxamer 181 | 0.020 |
| Glycerol | 0.50 |
| Erythritol | 0.50 |
| Purified Water | Q.S. to 100% w/w |

Example 3

An aqueous packaging solution was made by mixing the following components, listed in Table 3 at amounts per weight.

TABLE 3

| Ingredient | % w/w |
|---|---|
| Sodium Phosphate Monobasic Monohydrate | 0.00925 |
| Sodium Phosphate Dibasic Anhydrous | 0.0320 |
| Sodium chloride | 0.60 |
| Poloxamine 1107 | 0.550 |
| Poloxamer 181 | 0.020 |
| Glycerol | 0.90 |
| Erythritol | 0.90 |
| Purified Water | Q.S. to 100% w/w |

It will be understood that various modifications may be made to the embodiments disclosed herein. Therefore, the above description should not be construed as limiting, but merely as exemplifications of preferred embodiments. For example, the functions described above and implemented as the best mode for operating the illustrative non-limiting embodiments described herein are for illustration purposes only. Other arrangements and methods may be implemented by those skilled in the art without departing from the scope and spirit herein. Moreover, those skilled in the art will envision other modifications within the scope and spirit of the features and advantages appended hereto.

What is claimed is:

1. A packaging system for the storage of an ophthalmic device including a sealed container containing one or more unused ophthalmic devices immersed in an aqueous packaging solution consisting of:
   (a) erythritol;
   (b) one or more poloxamer comfort agents;
   (c) one or more polyol demulcents;
   (d) sodium chloride, potassium chloride or any combination thereof;
   (e) a poloxamine;
   (f) one or more buffers; and
   (g) water;
   wherein the aqueous packaging solution has an osmolality of at least about 150 mOsm/kg, a pH of about 6 to about 9 and is heat sterilized.
2. The packaging system of claim 1, wherein the ophthalmic device is a contact lens.
3. The packaging system of claim 1, wherein the one or more poloxamer comfort agents are one or more copolymers having poly(ethylene oxide)-poly(propylene oxide)-poly(ethylene oxide) blocks represented by the structure:

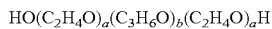

wherein a is independently at least 1 and b is at least 1.
4. The packaging system of claim 3, wherein the one or more copolymers have a hydrophilic-lipophilic balance (HLB) ranging from about 5 to about 24.
5. The packaging system of claim 1, wherein the one or more polyol demulcents is glycerol.
6. The packaging system of claim 1, wherein the aqueous packaging solution consists of:
   about 0.01% to about 10% w/w of erythritol;
   about 0.001 wt. % to about 5.0 wt. %, based on the total weight of the aqueous packaging solution, of the one or more poloxamer comfort agents; and
   about 0.01 to about 10.0 wt. %, based on the total weight of the aqueous packaging solution, of the one or more polyol demulcents.
7. The packaging system of claim 1, wherein the aqueous packaging solution consists of:
   0.1% to about 10% w/w of erythritol;
   about 0.01 wt. % to about 1.0 wt. %, based on the total weight of the aqueous packaging solution, of the one or more poloxamer comfort agents; and
   about 0.1 wt. % to about 3.0 wt. %, based on the total weight of the aqueous packaging solution, of the one or more polyol demulcents.
8. The packaging system of claim 1, wherein the aqueous packaging solution consists of:
   about 0.01 wt. % to about 5.0 wt. %, based on the total weight of the aqueous packaging solution, of erythritol;
   about 0.01 wt. % to about 1.0 wt. %, based on the total weight of the aqueous packaging solution, of the one or more poloxamer comfort agents; and
   about 0.1 wt. % to about 3.0 wt. %, based on the total weight of the aqueous packaging solution, of glycerol.
9. The packaging system of claim 1, wherein the sealed container is heat sterilized subsequent to sealing of the container.
10. The packaging system of claim 1, wherein the aqueous packaging solution consists of:
    about 0.01% to about 10% w/w of erythritol;
    about 0.001 wt. % to about 5.0 wt. %, based on the total weight of the aqueous packaging solution, of the one or more poloxamer comfort agents; and
    about 0.01 to about 10.0 wt. %, based on the total weight of the aqueous packaging solution, of glycerol;
    0.01 to about 2.5% w/v of the sodium chloride, potassium chloride or any combination thereof; and
    about 0.001 to about 5.0 wt. %, based on the total weight of the aqueous packaging solution, of the poloxamine.
11. The packaging system of claim 1, wherein the one or more buffers are one or more phosphate buffers.
12. The packaging system of claim 1, wherein the one or more buffers include sodium phosphate monobasic monohydrate and sodium phosphate dibasic anhydrous.
13. A method of preparing a package comprising a storable, sterile ophthalmic device, the method comprising consisting of:
    (a) immersing an ophthalmic device in an aqueous packaging solution consisting of:
        (i) erythritol,
        (ii) one or more poloxamer comfort agents,
        (iii) one or more polyol demulcents,
        (iv) sodium chloride, potassium chloride or any combination thereof, (v) a poloxamine,
(vi) one or more buffers, and
(vii) water;
wherein the aqueous packaging solution has an osmolality of at least about 150 mOsm/kg and a pH in the range of about 6 to about 9;
(b) packaging the aqueous packaging solution and the ophthalmic device in a manner preventing contamination of the ophthalmic device by microorganisms; and
(c) sterilizing the packaged aqueous packaging solution and the ophthalmic device.

14. The method of claim 13, wherein the ophthalmic device is a contact lens.

15. The method of claim 13, wherein the one or more poloxamer comfort agents are one or more copolymers having poly(ethylene oxide)-poly(propylene oxide)-poly(ethylene oxide) blocks represented by the structure:

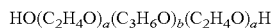

$HO(C_2H_4O)_a(C_3H_6O)_b(C_2H_4O)_aH$ wherein a is independently at least 1 and b is at least 1.

16. The method of claim 13, wherein the aqueous packaging solution consists of:
about 0.01% to about 10% w/w of erythritol;
about 0.001 wt. % to about 5.0 wt. %, based on the total weight of the aqueous packaging solution, of the one or more poloxamer comfort agents; and
about 0.1 wt. % to about 3.0 wt. %, based on the total weight of the aqueous packaging solution, of the one or more polyol demulcents.

17. The method of claim 13, wherein the one or more polyol demulcents is glycerol.

18. The method of claim 13, wherein the aqueous packaging solution consists of:
about 0.01% to about 10% w/w of erythritol;
about 0.001 wt. % to about 5.0 wt. %, based on the total weight of the aqueous packaging solution, of the one or more poloxamer comfort agents; and
about 0.01 to about 10.0 wt. %, based on the total weight of the aqueous packaging solution, of the one or more polyol demulcents.

19. The method of claim 13, wherein the aqueous packaging solution consists of:
about 0.1% to about 10% w/w of erythritol;
about 0.01 wt. % to about 1.0 wt. %, based on the total weight of the aqueous packaging solution, of the one or more poloxamer comfort agents; and
about 0.1 wt. % to about 3.0 wt. %, based on the total weight of the aqueous packaging solution, of the one or more polyol demulcents.

20. The method of claim 13, wherein the aqueous packaging solution consists of:
about 0.01 wt. % to about 5.0 wt. %, based on the total weight of the aqueous packaging solution, of erythritol;
about 0.01 wt. % to about 1.0 wt. %, based on the total weight of the aqueous packaging solution, of the one or more poloxamer comfort agents; and
about 0.1 wt. % to about 3.0 wt. %, based on the total weight of the aqueous packaging solution, of glycerol.

21. The method of claim 13, wherein the aqueous packaging solution consists of:
about 0.01% to about 10% w/w of erythritol;
about 0.001 wt. % to about 5.0 wt. %, based on the total weight of the aqueous packaging solution, of the one or more poloxamer comfort agents, and
about 0.01 to about 10.0 wt. %, based on the total weight of the aqueous packaging solution, of glycerol;
0.01 to about 2.5% w/v of the sodium chloride, potassium chloride or any combination thereof, and
about 0.001 to about 5.0 wt. %, based on the total weight of the aqueous packaging solution, of the poloxamine.

22. The method of claim 13, wherein the one or more buffers are one or more phosphate buffers.

* * * * *

UNITED STATES PATENT AND TRADEMARK OFFICE
CERTIFICATE OF CORRECTION

PATENT NO. : 12,097,295 B2
APPLICATION NO. : 17/398556
DATED : September 24, 2024
INVENTOR(S) : Vicki Barniak et al.

Page 1 of 1

It is certified that error appears in the above-identified patent and that said Letters Patent is hereby corrected as shown below:

In the Claims

Claim 13, Column 18, Lines 58-59, please delete "of preparing a package comprising a storable, sterile ophthalmic device, the method comprising"

Signed and Sealed this
Twenty-second Day of October, 2024

Katherine Kelly Vidal
*Director of the United States Patent and Trademark Office*